US009127786B1

(12) United States Patent
Arratia

(10) Patent No.: US 9,127,786 B1
(45) Date of Patent: Sep. 8, 2015

(54) VASCULAR SURGICAL CLAMP FOR HOLDING AND GUIDING GUIDE WIRE ON A STERILE FIELD

(71) Applicant: Anselmo Arratia, Pearland, TX (US)

(72) Inventor: Anselmo Arratia, Pearland, TX (US)

(*) Notice: Subject to any disclaimer, the term of this patent is extended or adjusted under 35 U.S.C. 154(b) by 2 days.

(21) Appl. No.: 14/269,838

(22) Filed: May 5, 2014

(51) Int. Cl.
*F16L 3/22* (2006.01)
*F16L 3/10* (2006.01)
*A61M 25/09* (2006.01)
*A61M 25/02* (2006.01)

(52) U.S. Cl.
CPC ............... *F16L 3/1033* (2013.01); *A61M 25/09* (2013.01); *A61M 2025/024* (2013.01); *A61M 2025/09125* (2013.01)

(58) Field of Classification Search
CPC ................... A61M 25/09; A61M 2025/09125; A61M 2025/024; F16L 3/1033
USPC ........ 248/62, 63, 68.1, 73, 74.1; 24/543, 616; 128/DIG. 26; 604/174, 180
See application file for complete search history.

(56) References Cited

U.S. PATENT DOCUMENTS

| 459,977 | A | | 9/1891 | Moller |
| D234,204 | S | * | 1/1975 | Miller ........................... D24/145 |
| 4,277,864 | A | | 7/1981 | Orson, Sr. |
| 4,347,998 | A | * | 9/1982 | Loree ............................ 248/68.1 |
| 4,390,019 | A | * | 6/1983 | LeVeen et al. ................ 606/158 |
| 4,896,465 | A | * | 1/1990 | Rhodes et al. ................ 451/523 |
| 4,897,082 | A | * | 1/1990 | Erskine ......................... 604/180 |
| D323,588 | S | | 2/1992 | Pelosi |
| 5,226,892 | A | | 7/1993 | Boswell |
| 5,560,138 | A | | 10/1996 | Dentsbier |
| 5,707,703 | A | | 1/1998 | Rothrum et al. |
| 5,815,894 | A | * | 10/1998 | Soriano ........................... 24/510 |
| 5,815,904 | A | | 10/1998 | Clubb et al. |
| 5,830,183 | A | | 11/1998 | Krieger |
| D459,977 | S | | 7/2002 | Byrnes et al. |
| 6,460,231 | B2 | | 10/2002 | Bourgerie |
| 6,826,811 | B2 | | 12/2004 | Adams |
| D522,850 | S | | 6/2006 | Mandel |
| D571,649 | S | | 6/2008 | Baker |
| 7,951,092 | B2 | | 5/2011 | Jones et al. |
| 8,366,638 | B2 | | 2/2013 | Teirstein |
| 8,523,824 | B2 | | 9/2013 | Teirstein et al. |

(Continued)

OTHER PUBLICATIONS

3m Cable Clamp with Urethane Foam Tape, for up to 6 layers of flat cable, part 3484-1000-Bulk; Allied Electronics.

*Primary Examiner* — Gwendolyn W. Baxter
(74) *Attorney, Agent, or Firm* — Parks & Associates, PC

(57) ABSTRACT

A cardiovascular surgical clamp used for retaining, identifying and positioning surgical wire for patients on a sterile field without wire injury. Opposing members with opposing recessed surfaces and back end portions are provided having removable compressible inserts with large flat matching surface areas inserted into the recesses of opposing members. The opposing members have spring/s located between them for driving them together and for manually opening them apart and have hinges formed on projecting struts for allowing simultaneous contact of the large flat matching surface areas of the removable compressible inserts for frictional engagement of wire without injury. The projecting struts of the opposing members provide guide wire surfaces proximate where hinges are formed for guiding wire there through. The opposing members and the projecting struts are moved from a closed to open position and back by compression or release of back end portions of the opposing members.

17 Claims, 8 Drawing Sheets

(56) References Cited

U.S. PATENT DOCUMENTS

2008/0076989 A1 3/2008 Hete et al.
2013/0061857 A1 3/2013 McNally et al.
2013/0192032 A1 8/2013 Huang

* cited by examiner

VASCULAR SURGICAL CLAMP FOR HOLDING AND GUIDING GUIDE WIRE ON A STERILE FIELD

BACKGROUND OF THE INVENTION

1. Field of the Invention

This present invention relates generally to a clamp device used in the field of cardiovascular procedures, which includes vessels of the coronary arteries and heart, for retaining, identifying and locating surgical wire, individual wires and or coils of wire without damage to the wire and wires for patients on a sterile field and providing guiding surfaces for moving a wire or wires there through in a surgical procedure without injury to the wire or wires being used in the patient.

2. Background of the Invention

In cardiovascular procedures, such as coronary artery procedures, the patient is laid out under a sterile drape and a sheath is inserted into the patient through a round opening in the sterile drape at a location such as the lower right or left groin area of the patient. During the procedure a guide wire is inserted through a sheath into the patient and has its proximal end moved to a location within the body of the patient to an area for the particular treatment. This wire or wires is used as a control delivery system for moving treatment devices, such as a balloon catheter, over the wire to the locations in the body of the patient and the distal end of the guide wire remains outside the patient's body on the sterile drape. Many times the guide wire must be moved back and forth into and out of the patient to find the specific location in the patient's body where the treatment is to occur. This whole length of guide wire must be retained on the sterile drape at all times to keep it sterile during the procedure. This means the distal end of the guide wire may have to be coiled and secured for retention on the sterile drape and maintained in an identified and fixed location to keep the proximal end of the guide wire in its proper location in the patient. However any retention device for the guide wires must not crimp or put a bend in the wire less the wire be rendered useless and have to be replaced which is not desired in a surgical procedure.

In some cases it is necessary to run more than one guide wire into the same sheath located in a patient because the second wire must be advanced to a secondary blood vessel which will receive treatment in the same surgical procedure as the primary vessel. In such a case it is important both to identify the location of the guide wires in the primary and secondary vessel which have received a primary and secondary wire inserted into their respective locations in the patient based on the distal ends outside the patient. This means that the distal end of the guide wires have to be identified as the primary wire or the secondary wire so that the procedure such as a balloon catheter intended for primary blockage in a blood vessel can receive the proper catheter and the secondary vessel can receive the proper balloon catheter for it or just be available for a different purpose. The distal end of each of these guide wires must be identified to prevent errors as to which location in the patient the proximal end of the wire is located, because in many cases the wires are the same gauge and look the same. Also the distance of the wires and the location of their proximal ends in the patient need to be determined as well for the proper wire for delivery of the surgical devices being implanted by distribution over the wires to be achieved. If the distal end of the wire or wires are fixed at a location on the surgical drape after the proximal end is properly located in the patient, then the proximal end of the wire will be in the same location in the patient if the clamp is in a fixed position on the sterile drape, which is another reason for locating the distal end of the wire in a fixed location on the sterile drape.

In all these cases, the wire or wires must be easy to release for manipulation both into and out of the patient and must provide reserve lengths of wire if that becomes necessary for running the wire or wires and the reserves of wire into the patient. The reserves of wire or wires must be coiled and stored on the sterile field. Also the wires must be retained in such way that they are easy to release from a coil or from a fixed position and then moved through guiding devices to prevent bending or crimping the wires in the process of moving them both into the patient and back outward of the patient for either relocation or adjustment of their location in the patient. This process of going from a fixed position coil of wire being secured in a clamp and then into a guiding device for threading the wire or wires there through has created clutter on the sterile field and has required additional time for the surgical team to move from the release of the coiled wires to its insertion through a guiding device for further insertion into a patient.

SUMMARY OF THE INVENTION

The present invention relates to a clamp device for use on a sterile surgical field during surgery for retaining and locating coils of surgical wire or individual wires used in surgery for patients without injury or crimping of the wire or wires while being held by the clamp. This invention also relates to providing a clamp which can provide both the clamping function and also a wire guiding function. The movement from a clamp function to wire guide function can be achieved easily from a wire or wires being clamped in the clamp to being inserted for wire guiding in the clamp assembly while being maintained on the sterile field of the sterile drape.

The clamp of this invention in some embodiments is composed of two opposing first and second members which have recessed surfaces defined by walls on the front end of the two opposing first and second members for receiving first and second removable compressible inserts into their recessed surfaces and struts projecting from the recessed surface side of the first and second members having apertures therein and a back end portion of the first and second members projecting behind the projecting struts. These two opposing first and second members are hinged together to face each other and have first and second removable compressible inserts inserted in recessed surfaces in facing relationship as well. The removable compressible inserts which have large flat frictional surfaces are brought to engagement with each other by a spring or springs fixed between the two members which drive them together. The two members and their removable compressible inserts are arranged so that the intersection of the two surfaces of the removable compressible inserts are substantially simultaneous and their engagement is over the whole flat large surfaces of the removable compressible inserts against the wire or wires being inserted therein and thus distributes the force of the closing evenly over the whole flat large surfaces which does not crimp or bend the wires or wire being retained.

The present invention also provides for preventing damage to the wire or wires being clamped by having the compressible insert members being thick enough to keep the wire or wires from coming in contact with the recessed surface of the first and second members when the compressible insert members are inserted into the recessed surface of the first and second members and they are not too thick or not too high at the plane of meeting to cause uneven pressure to be delivered by the contacting of the two surfaces of the first and second compressible insert members meeting. The two surfaces of the removable compressible inserts are thus brought to meet each other simultaneously upon their closing and distribute the forces evenly over the relatively large flat surface area of the first and second removable compressible inserts.

In fact that this invention provides for removable compressible inserts, allows for having readily sterilized surfaces with which to hold the wire available at all times and provides easy trade out of the removable compressible inserts during the surgical procedure if it becomes necessary.

This invention also provides that the plane of the hinge formed between first and second members is in line with the plane of the meeting of the two removable compressible inserts with the right thicknesses provides a hinged closing mechanism for allowing full and even contact of all the relatively large flat matching surface areas of the first and second removable compressible inserts without any first contact point of the surface or the last contact point of the surface generating any stress compression points which could contact the wire for injury and crimping of the wire or wires being clamped.

This invention also provides a hinge which is formed at aperture points on the projecting struts of said of the first and second members with the projecting struts having a length sufficient from the first and second members to provide a hinge being formed which will align with the plane of the meeting between the large flat surface areas of the first and second removable compressible inserts to provide for simultaneous meeting of the removable compressible inserts and for frictional engagement of the wire or wires without providing compression injury or crimping of the wires.

Further this invention provides for the hinged movement of the first and second members having recessed surfaces on the front of the first and second members and a back portion on the first and second members with a spring member positioned between the first and second members for driving the first and second members with removable compressible inserts to a closed position and then allows for the opening of said first and second members by compression of the spring. This compression of the spring can be achieved by compression of the back end portions of the first and second members which project behind the projecting struts by the fingers of one human hand.

Also the clamp of this invention provides for the locating of the clamp on the sterile field in a fixed manner without the penetration of the sterile field with the wire or wires retained without the wire or wires being crimped or injured. The manner of locating this clamp with its wire or wire coils is provided by an elevated flat surfaces located on either side of the clamp for receiving double-sided tape to be applied to the elevated flat surfaces and the other side of the tape being attached to the sterile field. Having two sides were either side can be used with readily available two-sided tape allows easy selection and exacting location by the surgical team performing the procedure of fixing the clamp to the sterile field. Also in this invention the elevated flat surfaces to which the double-sided tape is applied is in a plane which is equal to or the highest point on the clamp when the clamp is laid on the sterile drape. By having these elevated flat surface points being elevated to the highest point on the clamp there is no interference from the hand actuated part of the clamp to prevent a good tape connection to the sterile drape.

It is a further object of this invention to provide a clamp which can provide both the clamping function and also a wire guiding function and move a wire or wires from one function of being clamped in the clamp to being inserted for wire guiding in the clamp assembly. This is easily achieved by opening the clamp and moving the wire to the wire guiding surfaces of the clamp and then closing the clamp and guiding the wire in its movement either into or out of the patient all in the same device. This function is further achieved in the invention by providing guiding surfaces formed at and from surfaces provided on the hinge projecting struts of the first and second members. These surfaces of the first and second members which have projecting struts which join to form a hinge are provided in certain embodiments with carved out surfaces which come together and meet on the projecting struts of the first and second members to create a guiding surface on the clamp to which wire wires may be smoothly run or used in patients during surgery.

The present clamp of this invention also provides a reduced front profile for easy insertion into coils of surgical wire or a single wire for clamping them in place. This reduced profile is achieved in the substantially rectangular embodiment of the clamp by the front of the first and second members being provided with diagonal corners from a point on the front to the sides of the substantially rectangular shaped first and second member while still providing sufficient surface area between the first and second removable compressible inserts when inserted for providing sufficient and evenly applied friction to hold the wire or wires without pinching the wire or wires. This reduced profile is further enhanced by having the front of the first and second members sloped down and away from the elevated flat surfaces towards the front for providing addition reduced front profile for allowing easy insertion into a coil of wire so as to not catch on the wire or wires.

Also this invention provides a means of coding these clamps, such as by color coding them, to distinguish one wire from another wire being used in a patient at a different locations when two wires are entered through the same patient entry point for identifying the wire over which the surgical device such as a balloon catheter may be run and in identifying the secondary vessel into which the wire is run for providing a means of distinction between the wires by the clamps being different colors which would not otherwise be available based on the wires location on the sterile drape and being run through the same entry point in a patient.

A variety of additional advantage of the invention will be set forth in part in the description which follows, and in part will be obvious from the description, or may be learned by practice of the invention. The advantages of the invention will be realized and attained by means of the elements and combinations particular pointed out in the claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. A brief description of the drawings is as follows:

FIG. 9 is a partial side view of the back end portion of one of the clamps of this invention showing a first and second carved out surfaces in the projecting struts of the first and second members at the hinge formation for forming a guide wire surface through the clamp and a wire in phantom lines being placed for being run there through FIG. 10 is a partial side view of the back end portion of one of the clamps of this invention showing first and second wire guiding surfaces formed by the projecting struts of the first and second members at the hinge formation for forming a guide wire surface through the clamp and a wire in phantom lines being placed for being run there through

DETAILED DESCRIPTION OF AN EXEMPLARY EMBODIMENT

Figure 1A:
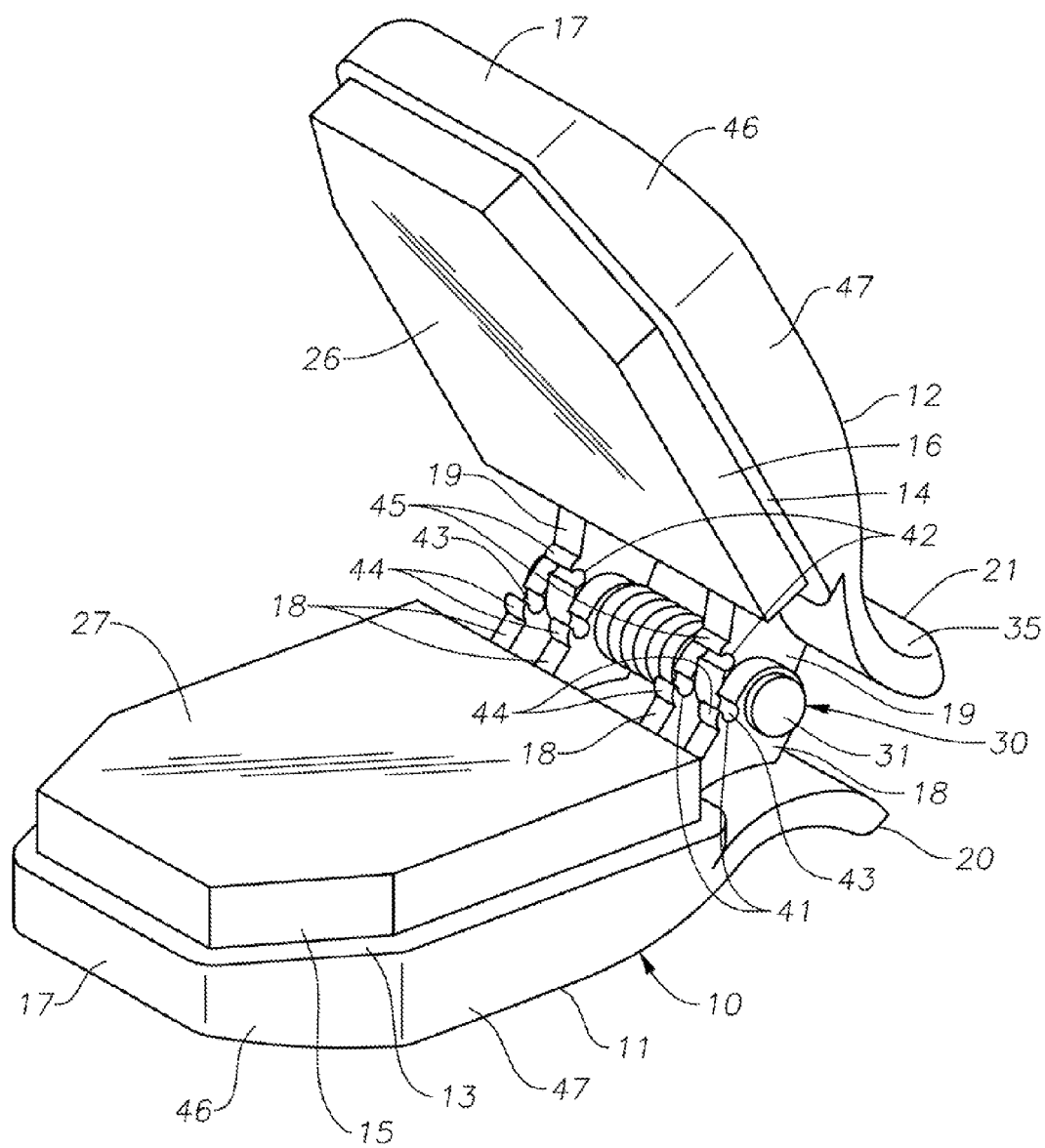
FIG. 1A is a perspective view of the clamp of this invention shown in an open position.

Reference will now be made in detail to exemplary embodiments of the present invention which are illustrated in the drawings. Whenever possible, the same reference numbers will be used throughout the drawings to refer to the same or like parts.

Figure 1B:
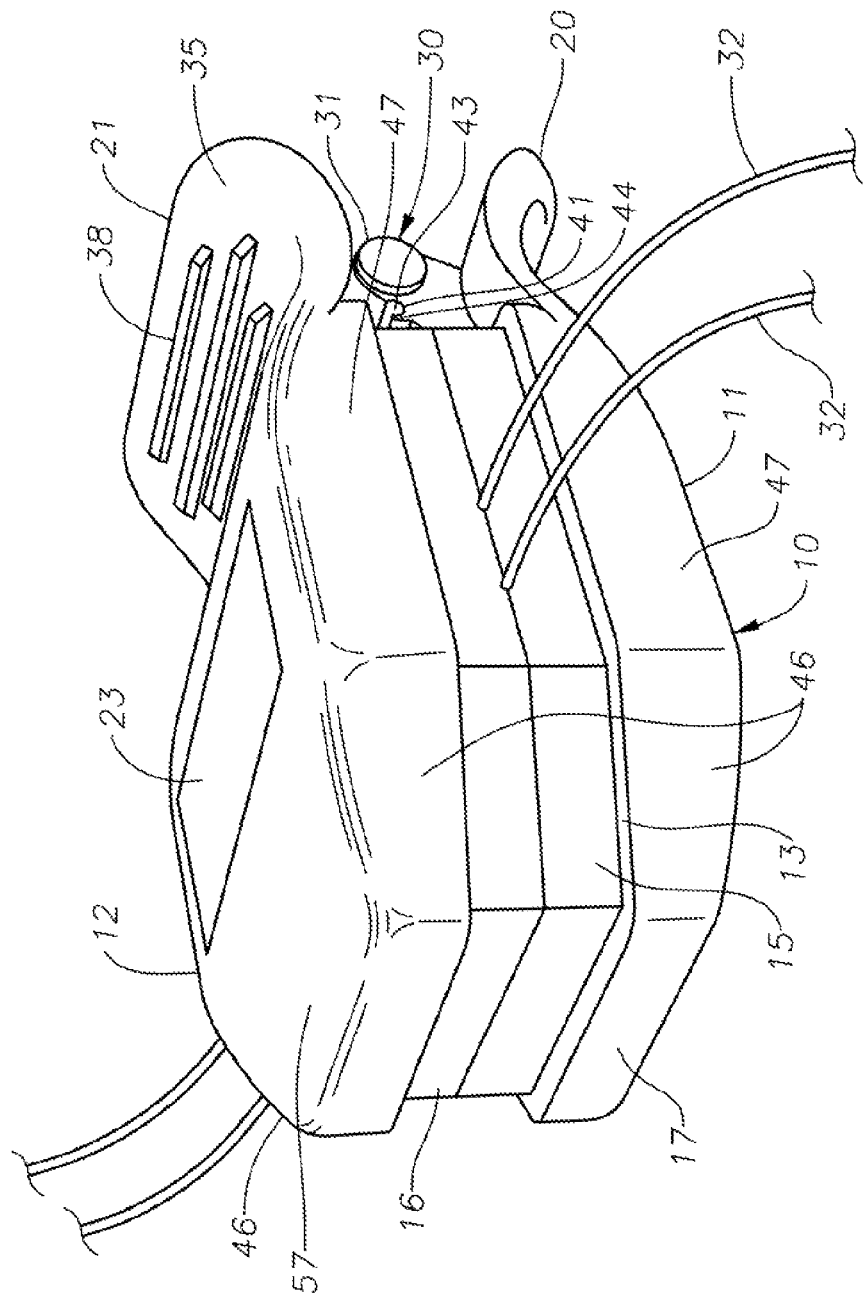
FIG. 1B is a perspective view of the clamp of this invention shown in the closed position retaining wires.

One example is shown in FIG. 1A and FIG. 1B of the surgical clamp 10 utilizing the principles of the present invention and while it is in a generally rectangular shape the clamp 10 can be any shape as long as it follows the principles of this present invention disclosed by the specification and claims. It will be appreciated that the surgical clamp 10 as shown in FIG. 1A and FIG. 1B are but examples of many forms of the surgical clamp 10 using the general principles of the present invention.

Figure 2:
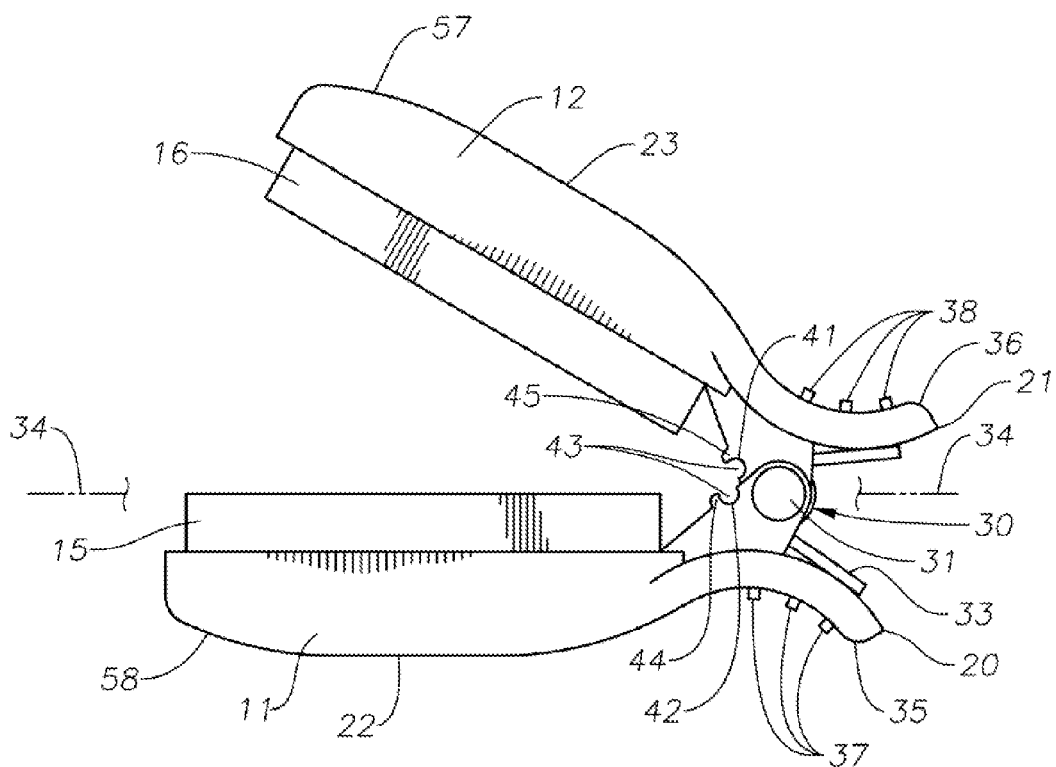
FIG. 2 is a side view with the clamp in open position.
Figure 3:
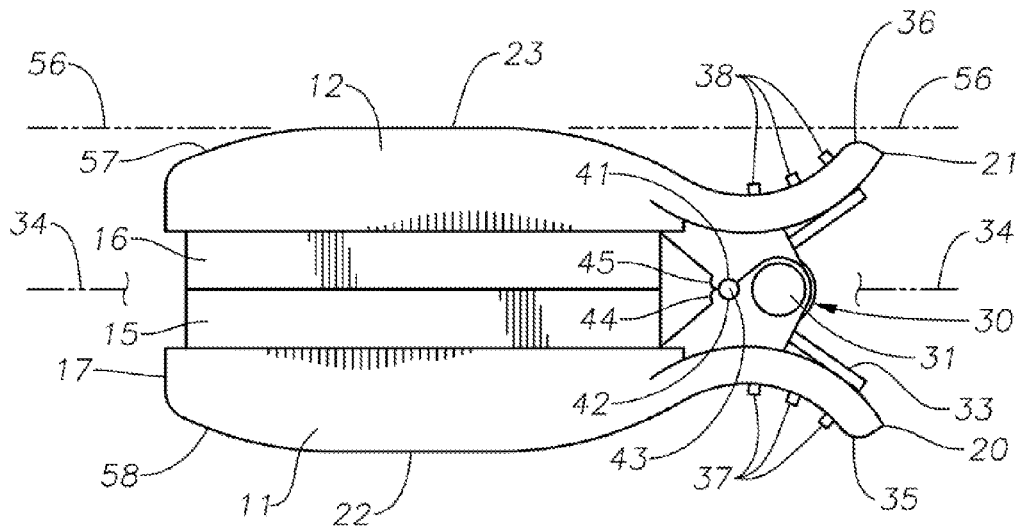
FIG. 3 is a side view with the clamp in a closed position.

The surgical clamp 10 in FIG. 1A shows in general a first member 11 and second member 12 which are in facing relationship with each other and which have in general a receiving surface 13 on first member 11 and a receiving surface 14 on the second member 12 for holding, as shown, a first removable compressible insert 15 and a second removable compressible insert 16 which are both located on the front 17 of the surgical clamp 10. Also seen in the FIG. 1A are projecting struts 18 which project from the receiving surface side of the first member 11 and projecting struts 19 which project from the receiving surface side of the second member 12. The first member 11 and second members 12 are completed by having a back end portion 20 and back end portion 21 which project behind the project projecting struts 18 and projecting struts 19 of the first and second member 11 and 12. Located on the first member 11 is an elevated flat surface 22 which is located opposite the receiving surface 13 of first member 11, but is not shown in FIG. 1A or FIG. 1B but may be seen from a side view in FIG. 2 and FIG. 3. A similar elevated flat surface 23 is provided which is opposite the receiving surface 14 of second member 12 and this elevated flat surface 22 is best shown in FIG. 1B. These elevated flat surfaces 22 and 23 are located midway of the receiving surfaces of 13 and 14 of first member and second member 11 and 12, as shown in FIG. 1B, FIG. 2, and FIG. 3, to provide even weight distribution of the clamp 10 over the surfaces of the flat surfaces 22 and 23 when either of these surfaces are laid on a flat surface.

Figure 4:
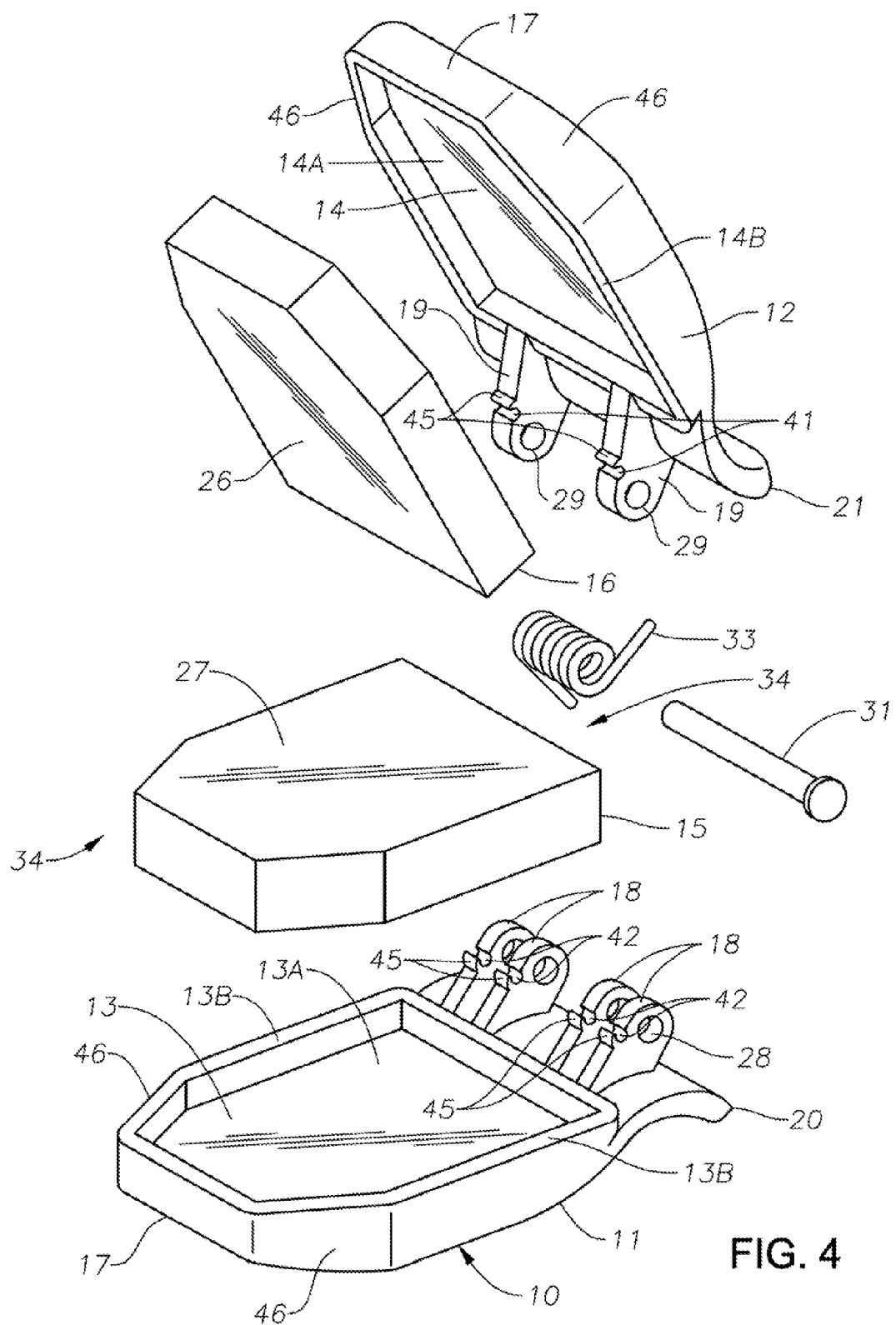
FIG. 4 is an exploded view of the clamp of this invention.
Figure 5:
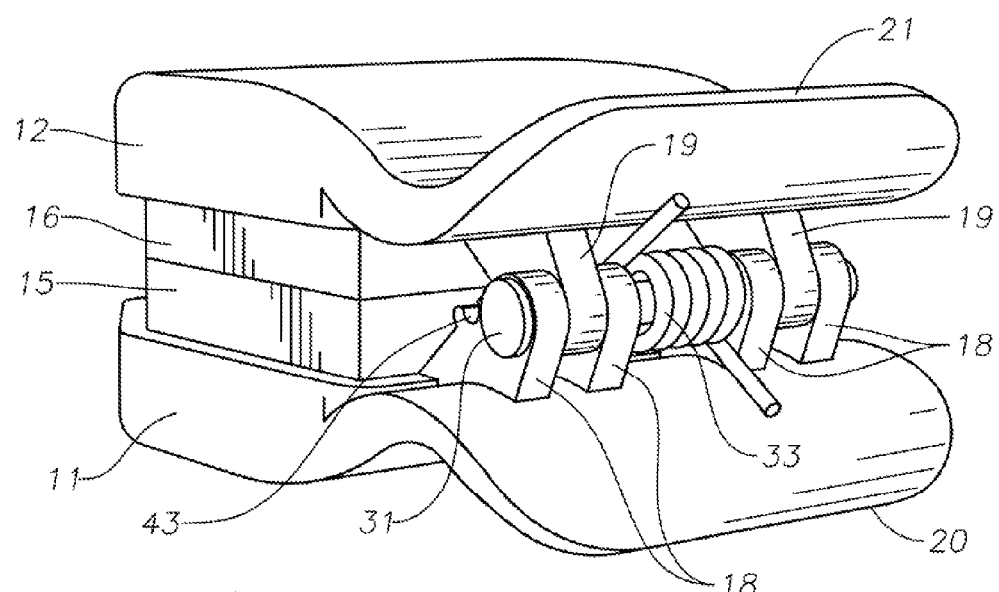
FIG. 5 is a perspective rear view of the clamp of this invention showing the back end portion with the hinge and spring.

The receiving surfaces 13 and 14 of first member 11 and second member 12 may be designed in many ways for holding the first removable compressible insert 15 and the second removable compressible answers 16 to be within the scope of this invention. In one embodiment, as shown in FIG. 4, the receiving surfaces 13 and 14 for receiving the first and second removable compressible inserts 15 and 16 are composed of a recessed surfaces 13A and 14A being defined by raised members 13B and 14B which take the form of raised walls which surrounds the recessed surfaces 13A and 14A for providing a means to retain the first and second removable compressible inserts 15 and 16 when they are inserted into the recessed surfaces 13A and 14A of the receiving surfaces 13 and 14. As the first and second removable compressible inserts 15 and 16 are designed to the slightly larger in size than the recessed surfaces 13A and 14A defined by raised members 13B and 14B the compressible nature of the first and second removable compressible inserts 15 and 16 cause them to be retained on insertion, but allow them to be easily removed by simply lifting them out of the receiving surfaces 13 and 14.

The first removable compressible insert 15 and the second removable compressible insert 16 which are provided for insertion into the receiving surfaces 13 and 14 of the first member 11 and the second member 12 are relatively thick and have relatively large flat surface areas 26 and 27, as shown in FIG. 1A and FIG. 4. The thickness of the first and second removable compressible inserts 15 and 16 must be thick enough to extend the relatively large flat surface areas 26 and 27 above the receiving surface 13 and 14 or raised members 13B and 14B of first and second members 11 and 12, but cannot be so thick or high as to not meet simultaneously and completely when the first and second members 11 and 12 are closed against each other. While these large flat surface areas 26 and 27 have compressible frictional surfaces for holding wire, they are designed and intended to match and meet at these relatively large flat surface areas 26 and 27 for holding wire, as shown in FIG. 1B without having any crimping forces caused by the surfaces not meeting evenly and simultaneously. Some examples of the materials used for the first and second removable compressible inserts 16 and 17 are foam materials which are compressible and have frictional surfaces.

To achieve the even and simultaneous closure of the first and second removable compressible insert 16 and 17 in some embodiments, as shown in FIG. 1A, but best shown in FIG. 4, projecting struts 18 of first member 11 and projecting struts 19 of second member 12 are provided which have apertures 28 on the projecting struts 18 of first member 11 and apertures 29 on the projecting strut 19 of second member 12 which may be aligned to form a hinge which is shown as a general reference hinge member 30. This hinge member 30 may in some embodiments be formed by at least one axle 31 being inserted through the aligned apertures 28 and 29 to form the hinge member 30. It should be appreciated that when hinge member 30 is formed at the apertures 28 and 29 of the projecting struts 18 in 19, that the projecting struts 18 and 19 must have sufficient length from the first and second members 11 and 12 for the hinge member 30 to be aligned for allowing full and even contact of all the large flat surface areas 26 and 27 of the first and second removable compressible inserts 15 and 16 and for allowing substantially simultaneous contact with each other for frictional engagement of a wire or wires without compression injury or crimping of the wire 32 as shown in FIG. 1B.

To make the clamp 10 operational a resilient member 33, such as a spring, may be positioned between the first member 11 and second member 12 for example at the formation of the hinge member 30, by placing the resilient member 33 over the axle 31, as shown in FIG. 4, for driving the first and second member 11 and 12 with the first and second removable compressible inserts 15 and 16 together when they are inserted in the receiving surfaces 13 and 14 of the first and second members 11 and 12. This positioning of the resilient member 33 at the hinge member 30, in this example, allows for the first and second members 11 and 12 with their respective first and second removable compressible inserts 15 and 16 to be articulated against the resilient member 33 from a closed position as shown in FIG. 1B to an open position as shown in FIG. 1A by compression of the back end portions 20 and 21 of the first and second members 11 and 12 and back to a closed position as shown in FIG. 1B by release of the back end portions 20 and 21 of first and second members 11 and 12 by the simple use of fingers of a human hand.

To make the back end portions 20 and 21 of first and second members 11 and 12 more readily operable by a single human hand, as shown in FIG. 1B, FIG. 2 and FIG. 3, the back end portion 20 of first member 11 is provided with a gripping surface 35 which turns up and away from the projecting strut 18 of first member 11 and the back end portion 21 of the second member 12 is provided with a gripping surface 36 which turns up and away from the projecting strut 19 of the second member 12. This configuration thus forms an actuator means for the surgical clamp 10 about the aligned projecting struts 18 and 19 at the hinge member 30 to allow easy operation by the fingers of a one human hand. In some embodiments of the surgical clamp 10 the gripping surfaces 35 and 36 are further provided with raised finger surfaces 37 and 38 on the back end portion 20 and 21 which further enhances the ability of fingers of one hand to be used in the operation of the clamp 10.

It should be appreciated in this example shown in FIG. 2 and FIG. 3 that the projecting struts 18 in 19 are of a sufficient length from the first and second members 11 and 12 for when aligning the apertures 28 and 29 to form a hinge member 30 that the hinge member 30 would be formed in alignment with the plane 34 of meeting between the large flat surface areas 26 and 27 of the first and second removable compressible inserts 15 and 16 for allowing the meeting to be substantially simultaneous and allowing frictional engagement of the wire 32, shown in FIG. 1B, without compression injury or crimping of the wire 32. To assist in achieving this the first and second removable compressible inserts 15 and 16 are just thick enough for matching of the alignment of the hinge member 30 in alignment with the plane 34 of the meeting between the first and second large flat surface areas 26 and 27 of the first and second compressible insert 15 and 16, as shown in FIG. 2 and FIG. 3. It should also be appreciated that first and second removable compressible inserts 15 and 16 must also have a thickness which rises above the receiving surface 13 and 14 of first members 11 and 12 to prevent contact with the wire 32 lest the wire be damaged by the receiving surface 13 and 14 of first and second members 11 and 12 when the clamp 10 is closed on the wire 32.

Figure 6:
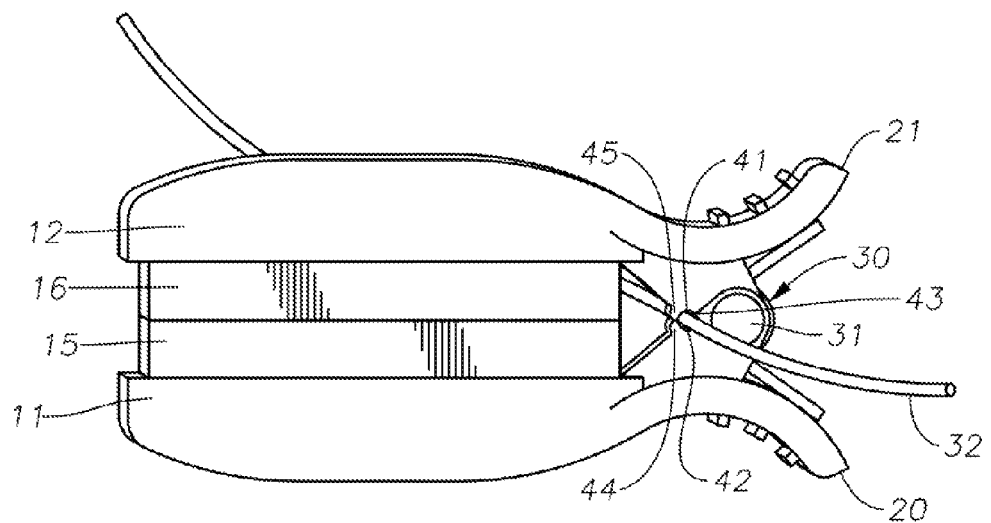
FIG. 6 is a view of the clamp of this invention showing wire fed along the guide surfaces on the struts.
Figure 9:
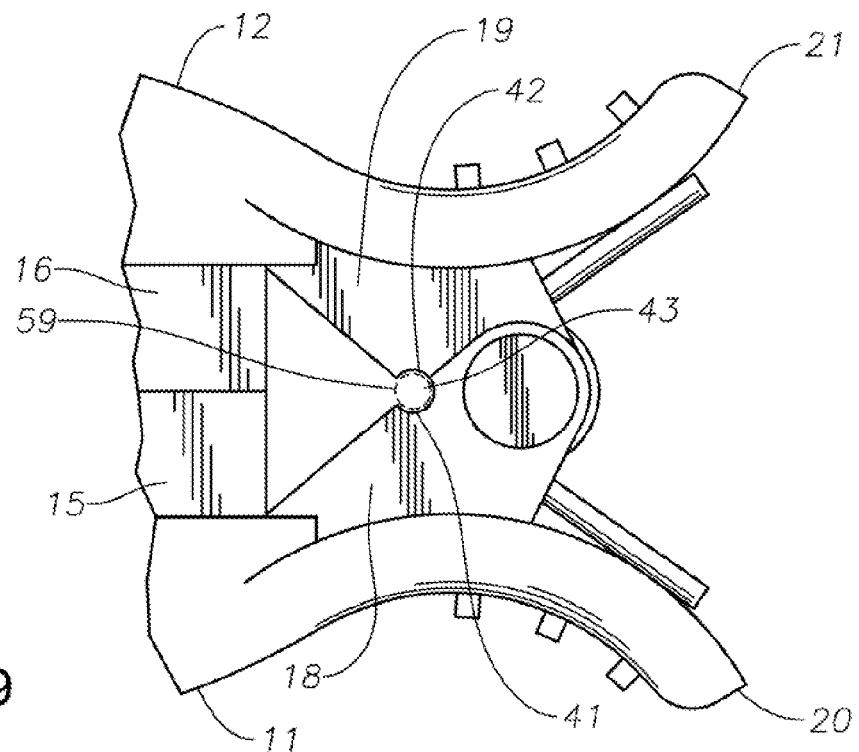
Figure 10:
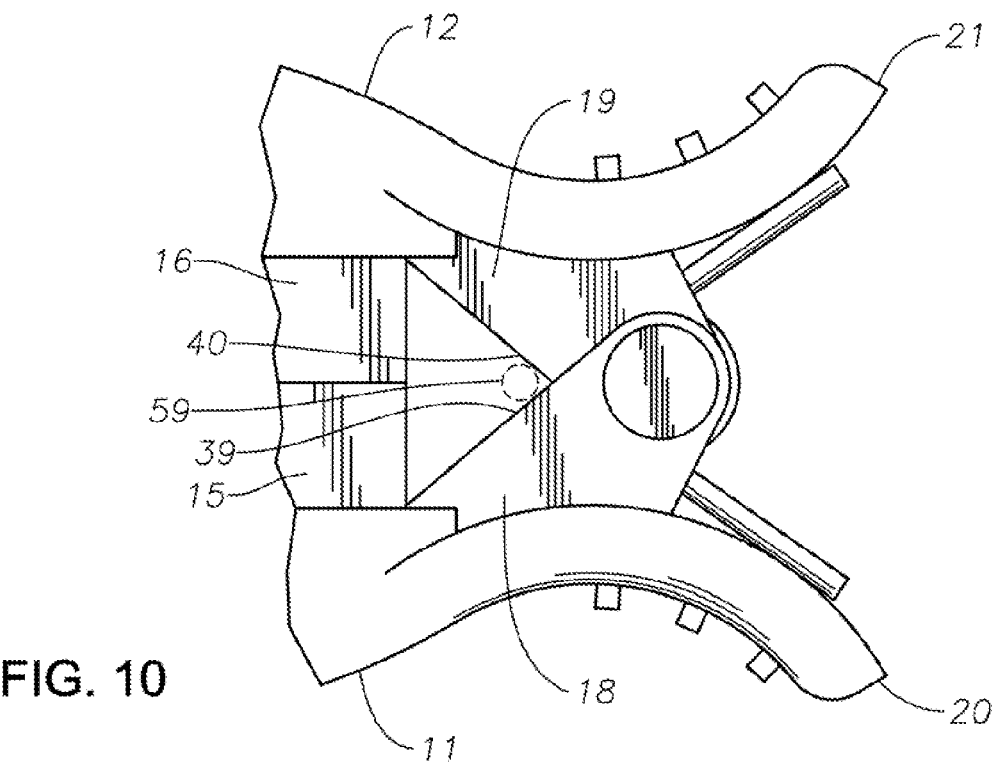

As those skilled in the vascular surgical arts will be aware, it is important not only to clamp wire or wires to hold position but it is also important for feeding wire into the patient in such a way that the wires are not being damaged. Thus it is important to be able to go from the process of wires being clamped to a process of wire guiding feed as easily and as smoothly as possible. In that regard the clamp 10 of this invention is provided with wire guiding surfaces 39 and 40 which are formed between a first wire guide surface 39 which is formed on the projecting strut 18 of first member 11 at the point of hinge member 30 formation and between the recessed surface 13 of the first member 11 and a second wire guide surface 40 which is formed on projecting strut 19 of the second member 12 where the two wire guiding surfaces 39 and 40 on their respective struts 18 in 19 meet just in front of the hinge member 30 formation, as best shown in FIG. 10, where a wire 59 in phantom lined cross-section is shown. In some embodiments the first and second wire guide surfaces 39 and 40 as shown in FIG. 9 are further enhanced by first carved out surface 41 being provided in place of the first wire guide surface 39 and a second carved out surface 42 being provided in place of second wire guide surface 40 such that in combination the first and second carved out surface 41 and 42 form a channel 43 which runs through all the projecting struts 18 and 19 to provide a smooth guiding surface for running wire or wires in the clamp 10. Other embodiments of wire guiding surfaces, as shown in FIGS. 2, 3, and 4, are also provided having a first curve surface projections 44 which extend from the first carved out surface 41 in the projecting struts 18 of the first member 11 and with second curved surface projections 45 which extend from the second carved out surfaces 42 in the projecting struts 19 of the second member 12 such that at the point of hinge formation the first and second curved surface projections 44 and 45 meet for forming a closed channel 43 when said clamp 10 is closed and are moved apart to open the channel 43 when the clamp is open for wire insertion or removal. Thus, it will be seen that a wire or wires can be smoothly moved from a clamped position to the channel 43 for advancing or retracting wire all on the same device with relative ease of access, as shown in FIG. 6, with the use of one hand.

Positioning of a clamp in a static position with ease is also important in vascular surgery because once a wire is positioned in a patient it is not desirable for the wire to be moved on its distal end which is on the sterile drape outside the patient because it may move from a set position in the patient. This is achieved, as shown in FIGS. 1B, 2 and 3, by providing the elevated flat surface 22 of first member 11 which is positioned opposite the receiving surface 13 and elevated flat surface 23 of second member 12 which is opposite the receiving surface 14 of the second member 12 being positioned midway over the receiving surface of the respective first and second members 11 and 12 for receiving two-sided tape being applied to either the elevated flat surface 22 or elevated flat surface 23 and then to the sterile drape 51. These elevated flat surfaces 22 and 23 are positioned in the same plane or a higher plane than any other surfaces on the first and second members 11 and 12 when the first and second members 11 and 12 are placed down on a sterile drape surface to be attached. Thus, as shown in FIG. 3 by plane line 56, either elevated flat surface 22 or 23 can be used for securing the clamp 10 to the sterile drape in surgery by attaching two-sided tape to one side of the elevated flat surfaces 22 or 23 and securing the other side of the tape to the sterile drape 51, but either side of the clamp 10 may be selected because it has two elevated flat surface 22 or 23 which provides ease of attachment. It should be understood by those skilled in the art that the elevated flat surfaces 22 and 23 of first and second members 11 and 12 are positioned in the same plane or a higher plane 56 than any other surfaces on the first member 11 or second member 12 when the first member or second members 11 and 12 are placed down on the sterile drape surface to be attached to it. Thus the elevated flat surfaces 22 and 23 of first and second member 11 and 12 are for example in a higher plane 56 than the tips of the gripping surfaces 35 and 36 of first and second members 11 and 12 so that there is no interference between the gripping surfaces 35 and 36 with the full surface area contact of the elevated flat surfaces 22 and 23 of first and second members 11 and 12 making contact with the sterile drape 51.

Clamp member 10 may take various shapes but no matter what shape it takes it must provide a reduced profile on the front end 17. In the case of rectangular shaped clamp member 10 as shown in FIG. 1B, the clamp member 10 is substantially a rectangular shape having a front end 17 and provided with diagonal corners 46 from one point on the front 17 to the sides 47 of the substantially rectangular clamp 10. The diagonal corners 46 on the substantially rectangular shape of clamp member 10 allows for easy insertion of clamp member 10 into coils of wire or wires because it reduces the profile of the clam member 10. Further reduction in the front profile of the first and second members 11 and 12 are achieved by providing the front 17 of the first and second members 11 and 12 with downward sloping surfaces 57 and 58 which slope down from the elevated flat surfaces 22 and 23 of first and second members 11 and 12. Thus the combined profile of diagonal corners 46 and downward sloping surfaces 57 and 58 from the elevated flat surfaces 22 and 23 of first members 11 and 12 provide a profile which is readily insertable into a coil of wire.

Figure 7:
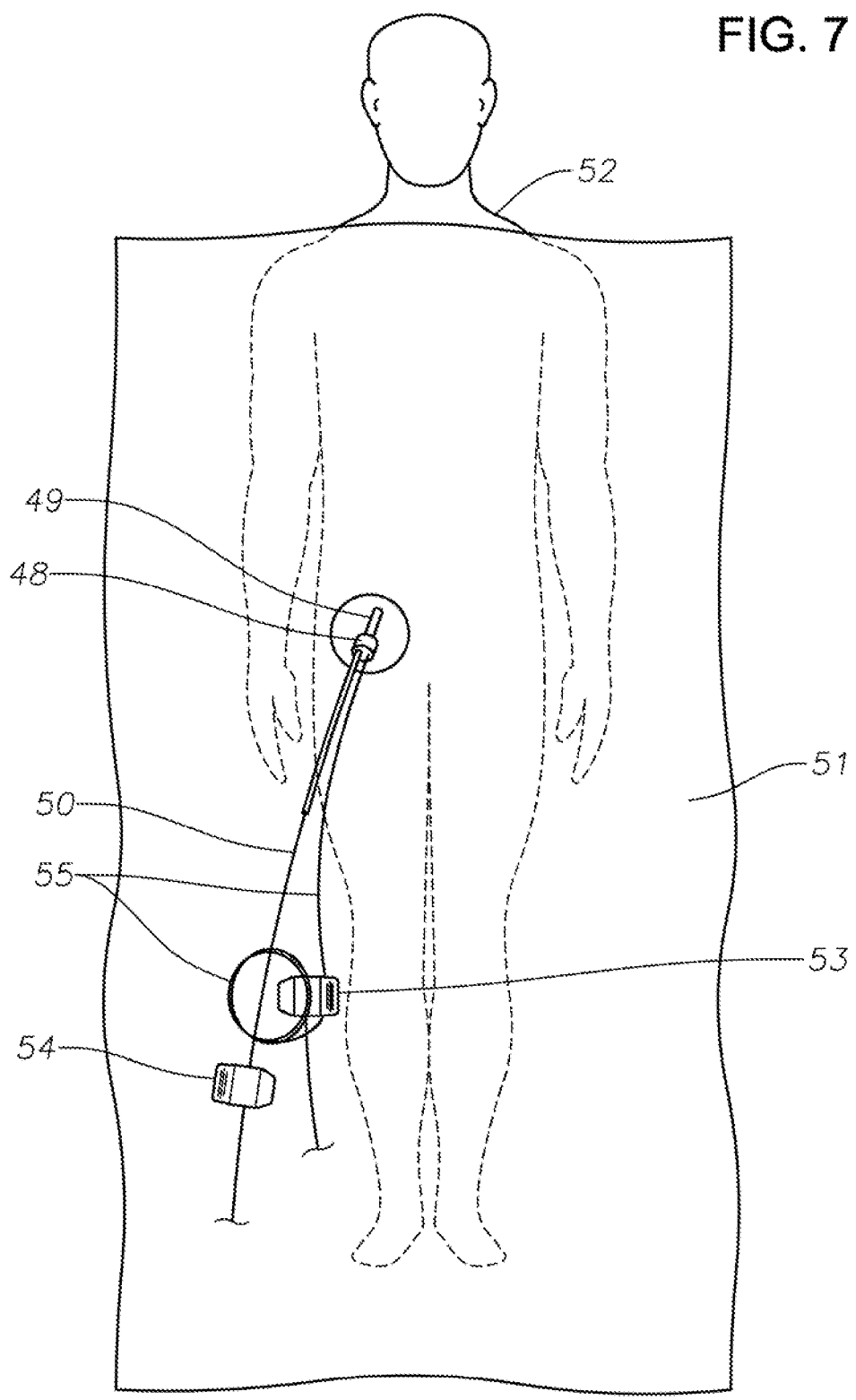
FIG. 7 is a plan view of a patient, showing the sterile drape, wires being run in a patient and the clamps being fastened to the sterile drape.
Figure 8:
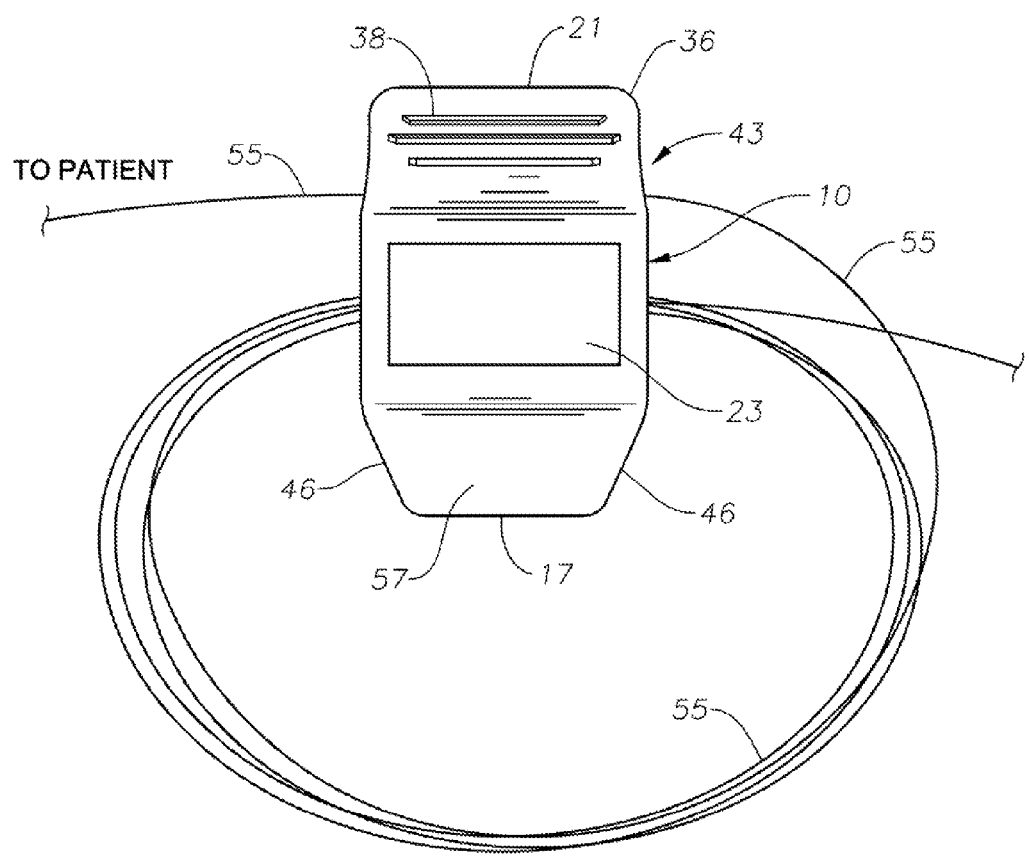
FIG. 8 is a top view of one of the clamps shown in FIG. 7 of this invention showing a coil of wire securely fastened by the clamp and showing a portion of the wire passed through the channel of wire guiding surfaces, and passed to a patient.

As those skilled in the art will well be aware there may be times when more than one guide wire will be run into a patient 52, as shown in FIG. 7, through the same sheath 48 located in the patient's groin 49 because the second wire 50 must be advanced to a secondary blood vessel which will receive treatment as well as the primary blood vessel. In such a case it is important both to identify the location of the guide wire in the primary and secondary vessels and which vessel has received the primary guide wire 55 and which has received the secondary guide wire 50. Also it is important to maintain the distal end of the primary guide wire 55 and secondary guide wire 50 of the guide wires on the sterile drape 51 after they had been positioned in the patient. As these wires are many times the same identical gauge it is important they be identified on the sterile drape 51 as to which one is the primary guide wire 55 or the secondary guide wire 50. In the application of the invention of this clamp 10, as shown in FIG. 7, the clamps 10 are provided a coding means, which in one example, as shown in FIG. 7, the clamps are provided in a series of colors such as red, yellow, and blue so that the primary guide wire 55 would have a red clamp 53 and the secondary wire 50 would have a blue clamp 54 on the sterile drape 51 for easy identification. Also it should be noticed that the red clamp 53 located with its distal end at one position on the sterile drape 51, which means its proximal end is at a fixed position in the patient, and blue Clamp 54 located with its distal end at a second position on the sterile drape 51, which means its proximal end is at a different fixed position in the patient than the wire of the red clamp 53, thus they are at different locations on the sterile drape 51. Thus once the respective red clamp 53 and blue clamp 54 are fixed to the sterile drape 51 by the double-sided tape, not shown, these wires are maintained in a fixed position in the patient while on the sterile drape 51 because they are held by the respective clamp in fixed locations. Also those skilled in the art will appreciate that red clamp 53, which is shown in FIG. 7 which has been magnified in FIG. 8 shows at least one interface between the clamping function of clamp 10 and its wire guiding function in that the primary guide wire 55 held by red clamp 53 shows a coil of wire, primary guide wire 55, held between the first and second removable compressible inserts 15 and 16 with the primary wire 55 passing through channels 43 formed at the meeting of first and second curve surface projections 44 and 45, though not visible, before passing from the clamp 10 to the sheath 48 and into the patient 52. This relationship is important as it shows how easily adjustments can be made using the clamp 10 of this invention in moving from a clamp wire position to feeding wire into or out of a patient 52 through the wire guiding function of the channel 43 of clamp 10.

With regard to the foregoing description, it is to be understood that changes may be made in detail, especially in matters of construction materials employed and the size, shape and arrangement of the parts without departing from the scope of the present invention. It is intended that the specification and depicted embodiment be considered exemplary only, with true scope and spirit of the invention being indicated by the broad meaning of the following claims.

The invention claimed is:

1. A surgical clamp for use on a sterile surgical field during surgery for retaining, locating and guiding coils of surgical wire or individual wires used in surgery for patients without injury or crimping of the wire or wires comprising:

a. a first member having a recessed surface on a front and an elevated flat surface on the top opposite a recessed surface side and struts projecting from said recessed surface side of said first member having apertures therein and a back end portion of said first member projecting behind said projecting struts, b. a second member, facing said recessed surface of said first member, having a recessed surface on a front and an elevated flat surface on the top opposite said recessed surface side and struts projecting from said recessed surface side of said second member having apertures therein and a back end portion of said second member projecting behind said projecting struts, c. a first removable compressible insert for insertion into said recessed surface of said first member having a frictional surface with a relative large flat surface area which extends above said recessed surface area of said first member after being inserted into said recessed surface on said first member, d. a second removable compressible insert for insertion into said recessed surface of said second member having a frictional surface with a relatively large flat surface area which matches and meets at said relative large flat surface area of said first removable insert which extends above said recessed surface area of said second member after being inserted into said recessed surface on said second member, e. a resilient member positioned between said first and second members for driving said first and second removable compressible inserts together when inserted in said recessed surfaces of said first and second members and f. a hinge member formed at said apertures of said projecting struts when said apertures of said struts of said first and second members are aligned for allowing full and even contact of said relatively large flat surface areas of said first and second removable compressible inserts and for allowing substantially simultaneous contact with each other for frictional engagement of wire or wires without compression injury or crimping of said wire or wires and for allowing said first and second members to be articulated against said resilient member from a closed to open position and back by compression or release of said back end portions of said first and second members projecting behind said projecting struts.

2. The surgical clamp of claim 1 wherein said hinge member formed at said apertures of said projecting struts of said first and second members further comprises, a. at least one axle inserted through said apertures on said projecting struts and b. said projecting struts have a length from said first and second members sufficient for when aligning said apertures to receive said axle for forming said hinge, said hinge is formed in alignment with the plane of said meeting between said large flat surfaces areas of said first and second removable compressible inserts for allowing said meeting to be substantially simultaneous and for frictional engagement of wire or wires without compression injury or crimping of said wire or wires.

3. The surgical clamp of claim 2 wherein said hinge member formed at said apertures of said projecting struts of said first and second members and said first and second removable compressible inserts further comprising, a. said first and second removable compressible inserts having a thickness which rises above said recessed surfaces of said first and second members to prevent contact with said wire or wires and are just thick enough for matching said hinge formation alignment with said plane of said meeting between said large flat surfaces areas of said first and second removable compressible inserts for providing full and simultaneous contact between said large flat surfaces of said first and second removable compressible inserts and maximum frictional engagement of wire or wires over the whole large flat surfaces of said first and second removable compressible inserts without crimping compression of said wire or wires when said first and second large flat surface areas of said first and second removable compressible inserts meet upon the closing of said first and second members.

4. The surgical Clamp of claim 3 wherein said back end portion of said first and second members projecting behind said projecting struts further comprises;

a. a gripping surface on said back end portion of said first member and said back portion turns up and away from said projecting struts, and b. said gripping surface on said back end portion of said second member and said back end portion turns up and away from said projecting strut in opposition to said gripping surface on said back end portion of said first member for forming an actuator means for said surgical clamp about said aligned struts forming said hinge.

5. The surgical Clamp of claim 4 wherein said projecting struts from said first and second members further comprises;

a. a first wire guiding surface formed on said projecting struts of said first member at said hinge formation and between said recessed surfaces of said first and second members, and b. a second wire guiding surface formed on said projecting struts of said second member at said hinge formation and between said recessed surfaces of said first and second members for forming in conjunction with said first wire guiding surface formed a guide wire surface for said wire.

6. The surgical Clamp of claim 5 wherein said guide wire surface between said projecting struts from said first and second members further comprises;

a. a first carved out surface in said projecting strut of said first member at said hinge formation and between said recessed surface of said first members and b. a second carved out surface in said projecting strut of said second member at said hinge formation and between said recessed surface of said second member which meets with said first carved out surface in said projecting strut of said first member at said hinge for forming in conjunction with said first carved out surface said guide wire surface through said clamp for wire run.

7. The surgical Clamp of claim 6 wherein said first and second wire guiding surfaces having first and second carved out surfaces formed on said projecting struts of said first and second members at said hinge formation further comprises;

a. first curved surface projections which extend from said first carved out surface in said projecting struts of said first member at said hinge formation and between said recessed surface of said first member, and b. second curved surface projections which extend from said second carved out surfaces in said projecting struts of said second member at said hinge formation and between said recessed surface of said second member and which meets with said first curved surface projections from said curved out surfaces in said projecting struts of said first member at said hinge for forming a closed channel for guiding wire through said clamp when said clamp is closed and are moved apart to open said channel when said clamp is opened for wire insertion or removal.

8. The surgical Clamp of claim 7 wherein said elevated flat surfaces on said top of said first and second members further comprises;

a. said elevated flat surface of said first member being positioned mid-way of said receiving surface below in said first member of said surgical clamp for receiving two sided tape on said clamp and b. said elevated flat surface of said second member being positioned mid-way of said receiving surface below in said second member of said surgical clamp for receiving two sided tape on said clamp which allows for either one or the other said elevated flat surfaces of said first and second members to be available for taped fastening to said sterile drape used in surgery to secure the surgical clamp to said drape for keeping said clamp and it wire contents stationary on said sterile drape in surgery.

9. The surgical Clamp of claim 8 wherein said elevated flat surfaces on said top of said first and second members further comprises;

a. said elevated flat surface of said first member is in the same plane or a higher plane than any other surfaces on said first member when said first member is placed down on a sterile drape surface to be attached and b. said elevated flat surface of said second member is in the same plane or a higher plane than any other surfaces on said second member when said second member is placed down on a sterile drape surface to be attached.

10. The surgical Clamp of claim 9 wherein said first and second members having said recessed surfaces on said front and elevated flat surfaces on said top opposite said recessed surface side and struts projecting from said recessed surface side of said first and second members having said apertures therein and a said back end portion of said first and second members projecting behind said projecting struts further comprise;

a. said first member which is substantially a rectangular shape having said front of said rectangular shape provided with diagonal corners from a point on said front to the sides of said substantially rectangular shaped first member having sufficient surface area between said first removable compressible inserts when inserted for providing sufficient and evenly applied friction to hold said wire or wires without pinching said wire or wires and allowing for easy insertion into a coil of wire, and b. said second member which is substantially a rectangular shape having said front of said rectangular shape provided with diagonal corners from a point on said front to the sides of said substantially rectangular shaped second member having sufficient surface area between said second removable compressible inserts when inserted for providing sufficient and evenly applied friction to hold said wire or wires without pinching said wire or wires and allowing for easy insertion into a coil of wire.

11. The surgical Clamp of claim 10 wherein said first and second members having said elevated flat surfaces on said top of said first and second members further comprises,
   a. a reduced front profile of said first and second members by having said front of said first and second members sloped down and away from said elevated flat surface towards said front for providing said reduced front profile for allowing easy insertion into a coil of wire so as to not catch on said wire or wires.

12. The surgical clamp of claim 11 wherein said back end portion of said first and second members projecting behind said projecting struts having gripping surfaces on said back end portions of said first and second members further comprises;
   a. raised finger surfaces on said gripping surfaces on said back end portion of said first member, and
   b. raised finger surfaces on said gripping surfaces on said back end portion of said second member for providing improved hand gripping of said surgical clamp for actuation thereof in conjunction with said raised finger surfaces on said gripping surfaces of said first member.

13. The surgical Clamp of claim 12 wherein said first and second members further comprise,
   a. a coding means for said first and second members of said clamp to identify the wire or wires being used in the patient during surgery.

14. The surgical Clamp of claim 13 wherein said coding means of said first and second members further comprise,
   a. color coding said first and second members of said surgical clamp for allowing one color clamp to identify a wire being used for one function on a patient and another color clamp to identify another wire being used for another function on said patient in surgery.

15. The surgical Clamp of claim 14 wherein said first and second removable compressible inserts having a frictional surface further comprises;
   a. said first removable compressible insert having a frictional surface which substantially follows and fills said first recessed surface of said first member, and
   b. said second removable compressible insert having a frictional surface which substantially follows and fills said second recessed surface of said second member.

16. The surgical clamp of claim 15 wherein said first carved out surfaces in said projecting struts of said first member at said hinge formation and between said recessed surface of said first member and said second carved out surfaces in said projecting struts of said second member at said hinge formation and between said recessed surface of said second member further comprises;
   a. said curved surface projections from said projecting struts at said first carved out surfaces on said first member, and
   b. said curved surface projections from said projecting struts at said second carved out surfaces on said second member for forming a wire guide in conjunction with said curved surface projections from said projecting struts on said first member for smoothly moving a wire there through in a surgical procedure.

17. The surgical clamp of claim 16 wherein said curved surface projections from said projecting struts on said first member and said curved surface projections from said projecting struts on said second member for forming a complete wire guiding surface in conjunction with said curved surface projections on said projecting struts on said first member at said hinge member further comprises;
   a. said curved surface projections which extend out from said cut out surfaces and which extend out from said projecting struts on said first member, and
   b. said curved surface projections which extend out from said cut out surfaces and which extends out from said projecting struts on said second member for forming said complete wire guiding surface when said first and second projecting struts are in said closed position with said first and second members in conjunction with said curved surface projection from said cut out surfaces on said projecting strut on said first member for allowing smoothly moving said wire there through in a surgical procedure and opens when said first and second projecting struts are in said open position with said first and second members in conjunction with said curved surface projection from said cut out surface on said projecting struts on said first member for smoothly removing said wire there from in said surgical procedure.

* * * * *